United States Patent
Shin et al.

(10) Patent No.: US 6,232,438 B1
(45) Date of Patent: May 15, 2001

(54) ANGIOTENSIN CONVERTING ENZYME INHIBITORS

(75) Inventors: Jae Ik Shin, Incheon; Hyung Jae Lee; Hyung Joo Lee, both of Seoul; Hee Sop Nam, Kyunggi-do; Chang Won Ahn, Incheon, all of (KR)

(73) Assignee: Nong Shim Co., Ltd., Seoul (KR)

( * ) Notice: Subject to any disclaimer, the term of this patent is extended or adjusted under 35 U.S.C. 154(b) by 0 days.

(21) Appl. No.: 09/101,503

(22) PCT Filed: Jan. 9, 1997

(86) PCT No.: PCT/KR97/00003

§ 371 Date: Jul. 10, 1998

§ 102(e) Date: Jul. 10, 1998

(87) PCT Pub. No.: WO97/25418

PCT Pub. Date: Jul. 17, 1997

(30) Foreign Application Priority Data

Jan. 11, 1996 (KR) .................................................. 96/411

(51) Int. Cl.⁷ .................................................. C07K 5/078
(52) U.S. Cl. .............................................. 530/331; 514/18
(58) Field of Search ..................... 514/18, 19; 530/331

(56) References Cited

U.S. PATENT DOCUMENTS

| | | | |
|---|---|---|---|
| 4,276,378 | 6/1981 | Ryan et al. | 435/23 |
| 4,666,884 * | 5/1987 | Hawiger | 514/13 |

FOREIGN PATENT DOCUMENTS

| | | |
|---|---|---|
| 0 583074A2 | 2/1994 | (EP) . |
| 62-169732 | 7/1987 | (JP) . |
| 62-270533 | 11/1987 | (JP) . |
| 64-5497 | 1/1989 | (JP) . |
| 64-83096 | 3/1989 | (JP) . |
| 3-167198 | 7/1991 | (JP) . |
| 4-299991 | 10/1992 | (JP) . |

OTHER PUBLICATIONS

Derwent Abstract of JP–01005497 A, 1989.*
Derwent Abstract of JP–62270533 A, 1987.*
Derwent Abstract of JP–62169732 A, 1987.*
Derwent Abstract of JP–04299991 A, 1992.*
Derwent Abstract of JP–03167198 A, 1991.*
Derwent Abstract of JP–01083096 A, 1989.*
Stein, Hoppe–Seyler's Z. Physiol. Chem. 349 472, 1968.*

* cited by examiner

*Primary Examiner*—Christopher S. F. Low
*Assistant Examiner*—David Lukton
(74) *Attorney, Agent, or Firm*—Jacobson, Price, Holman & Stern, PLLC

(57) ABSTRACT

An angiotensin converting enzyme inhibitor derived from foodstuff with high activity and high safety, suitable for mass production, having the formula (1) His-His-Leu or (2) His-Leu-Leu and physiologically acceptable salts thereof.

15 Claims, 2 Drawing Sheets

ANGIOTENSIN CONVERTING ENZYME INHIBITORS

FIELD OF THE INVENTION

The present invention relates to an angiotensin converting enzyme (referred to herein as "ACE") inhibitor, which prevent ACE from converting angiotensin-I to angiotensin-II, and more particularly to a safe ACE inhibitor derived from foodstuff.

BACKGROUND ART

The ACE acts on converting angiotensin-I to angiotensin-II. Angiotensin-II increases blood pressure and is considered a main cause of essential hypertension. A variety of studies have been directed to substances inhibiting ACE actions, whereby to suppress blood pressure rise.

Therapeutic vasodepressors such as Captopril and D-2-methyl-3-mercaptopropanoyl-L-proline have been synthesized as ACE inhibitors. From foodstuff, peptides having ACE inhibiting activities have been separated through enzymatic hydrolysis of casein [Japanese Laid-Open Patent Publication Nos. 62-270533, 64-5497, 64-83096] and soybean protein[Japanese Laid-Open Patent Publication Nos. 3-1671981].

Synthetic ACE inhibitors exhibit strong activities, however, they have adverse effects in many cases and generally are not considered safe. ACE inhibitory Peptides derived from casein or soybean protein have been developed with expectation of low toxicity and high safety, even though they exhibit low activities. Recent studies, therefore, have been focused on separating ACE inhibitors from foodstuff materials and manufacturing them on a large scale by chemical synthetic methods.

An ACE inhibitor derived from food protein was first reported in 1979 by Oshima et al [Oshima, G., Shimabukuro, H. and Nagasawa, K.: Peptide inhibitors of angiotensin-I converting enzyme in digests of gelatin by bacterial collagenase. Biochim. Biophys. Acta., 556. 128 (1979)].

Oshima et al obtained 9 peptides consisting of 3 to 12 amino acid residues by hydrolyzing gelatin for 24 hours with collagenase from *Clostridium histolyricum*. Of those, 6 peptides having alanine-hydroxyproline at their C-terminal end exhibit relatively high ACE inhibiting activities($IC_{50}$= 8.3–37 $\mu$M), while those having proline-X at the C-terminal end exhibit relatively low ACE inhibiting activities($IC_{50}$= 123.4–146.5 $\mu$M).

Since then over 40 ACE inhibitory Peptides have been disclosed to date [Ariyoshi, Y.: Angiotensin converting enzyme inhibitors derived from food proteins. Trend in Food Science & Technol., May, 139(1993)].

From enzymatic hydrolysate of milk casein, a peptide having a amino acid sequence of phenylalanine-phenylalanine-valine-alanine-proline-phenylalanine-proline-glutamic acid-valine-phenylalanine-glycine-lycine corresponding to 23–34 residues of α-casein B, a pentapeptide of phenylalanine-phenylalanine-valine-alanine-proline ($IC_{50}$=6.0 $\mu$M) [Maruyama, S. and Suzuki, H.: A peptide inhibitor of angiotensin-I converting enzyme in the tryptic hydrolysate of casein. Agric, Biol. Chem., 46(5), 1393 (1982)] and a heptapeptide of alanine-valine-proline-tyrosine-proline-glutamine-arginine, an equivalent of 177–183 residues of β-casein [Maruyama, S. Nakagomi, K., Tomizuka, N. and Suzuki, H.: Angiotensin-I converting enzyme inhibitor derived from an enzymatic hydrolysate of casein. II. Isolation and bradykinin potentiating activity on the uterus and the ileum of rats. Agric. Biol. Chem., 49(5), 1405(1985)] have been identified as ACE inhibitors. Based on the pentapeptide of phenylalariine-phenylalanine-valine-alanine-proline, a series of peptides with different amino acid sequences have been synthesized; valine-alanine-proline, phenylalanine-valine-alanine-proline, phenylalanine-alanine-proline with ACE inhibiting activities similar to that of parent pentapeptides[Kohmura, M., Nio, N. and Aryoshi, Y.: Inhibition of angiotensin converting enzyme by synthetic peptide fragments of various β-caseins. Agric. Biol, Chem., 54(4), 1101(1990)].

In enzymatic α-zein hydrolysate, three more ACE inhibitory peptides such as leucine-arginine-proline were reported [Miyoshi, S., Kaneko, T., Ishizawa, Y., Fukui, F., Tanaka, H. and Maruyama, S.: Structures and activity of angiotensin converting enzyme inhibitors in α-zein hydrolysate. Agric. Biol. Chem., 55(5), 1221(1991): Miyoshi, S., Kaneko, T., Ishizawa, Y., Fukui, F., Tanaka, H. and Maruyama, S.: Hypertensive activity of enzymatic α-zein hydrolysate. Agric. Biol. Chem., 55(5), 1407(1991)].

Other ACE inhibitory peptides have been derived from foodstuff such as sour milk [Nakamura, Y. Yamamoto, N., Sakai, K., Okubo, A., Yamazaki, S. and Takano, T.: Purification and characterization of angiotensin-I converting enzyme inhibitors from sour milk. J. Dairy Sci., 78, 777 (1995)], tuna tissue [Kohama, Y., Matsumoto, S., Oka, H., Teramoto, T., Okabe, M. and Mimura, T.: Isolation of angiotensin converting enzyme inhibitor from tuna muscle. Biochem. Biophys. Res. Comm., 155(1), 332(1988)], sardine muscle [Matsuda, H., Ishizaki, T., Moritam H., Nagaoka, T., Osajima, K. and Osajima, N.: Digestion of peptides from sardine muscle that inhibit angiotensin-I converting enzyme by intestinal enzyme of pigs. Nippon Nogeigaku Kaishi, 66(11), 1645(1992)], oyster protein [Matsumoto, K., Ogikubo, A., Yoshino, T., Matsui, T. and Osajima, Y.: Separation and purification of angiotensin-I converting enzyme inhibitory peptides in peptic hydrolyzate of oyster. Nippon Shokuhin Kogyo Gakkaishi, 41(9), 589 (1994)], *Ficus carica* [Maruyama, S., Miyosh, S. and Tanaka, H.: Angiotensin-I converting enzyme inhibitors derived from *Ficus carica*. Agric. Biol. Chem., 53(10), 2763(1989)], rice [Muramoto, M., Kawamora, Y., Rice protein and anti-hypertensive peptides derived from rice protein. Food Ind. 34(11), 18(1991)], sake and its by products [Saito, Y., Nakamura, K., Kawato, A., and Imayasu, S.: Angiotensin-I converting enzyme inhibitor in sake and its by-product. Nippon Nogeigaku Kaishi, 66(7)], etc.

Furthermore, numerous patent applications have been filed in relation with ACE inhibitory peptides from tri- to nona-: U.S. Pat. Nos. 5449661, 5071955, 4692459, 4585758, 4512979, 4191753, 3832337; EP174162; Japanese Laid-Open Patent Publication Nos. 8-225593, 8-099994, 6-340692, 6-298794, 6-279491, 6-279490, 6-277091, 6-277090, 6-277089, 6-256387, 6-220088, 6-184191, 6-166697, 6-107686, 6-049096, 6-016568, 5-306296, 5-306295, 5-294844, 5-262790, 5-097798, 5-001095, 4-341193, 4-300894, 4-282398, 4-279597, 4-264096, 4-264095, 4-247100, 4-247099, 4-247098, 4-169598, 3-063295, 3-011097.

DISCLOSURE OF THE INVENTION

In search of novel ACE inhibitory peptides with high activity and high safety, suitable for mass production, various foodstuffs were screened. Among those, we have found and separated two tri-peptides from fermented soybean paste, which meet the requirements satisfactorily.

Thus, it is an object of the present invention to provide a novel ACE inhibitor which exhibits excellent activities in controlling hypertension.

It is another object of the invention to provide an ACE inhibitor derived from foodstuff, safe when administered to human, with a simple structure suitable for mass production.

According to the invention, there is provided an angiotensin converting enzyme inhibitor with the structure;

[1] His-His-Leu;
[2] His-Leu-Leu and physiologically acceptable salts thereof.

The present invention will be described in more detail hereinbelow.

The peptides [1] and [2] according to the present invention are in the L-form as being naturally occurring, and may be produced by a conventional method of separating peptides from fermented soybean paste. Or they may be produced by an organochemical method known for peptide synthesis.

The physiologically acceptable salts of the peptides according to the invention may be employed as the ACE inhibitor, preferably inorganic acid salts such as hydrochlorides, hydrogen chloride acid salt, hydrogen iodide acid salts, sulfates, and organic acid salts such as acetates, citrates, tartrates, lactates, methanesulfonates.

The tri-peptides according to the present invention and physiologically acceptable salts thereof exhibit similar or higher activities when compared with known ACE inhibitory peptides, and they are safe since they are derived from foodstuff, Furthermore, their structures are simple enough and suitable for mass production.

A more complete appreciation of the present invention will be realized by reference to the following examples. The following examples are not intended to limit the invention disclosed herein but given only by way of illustration.

EXAMPLES

A. Separation of His-His-Leu and His-Leu-Leu from Fermented Soybean Paste

Fermented soybean paste was freeze-dried and then powdered. 300 g of the powder was put in 5 l-extraction bath, and 3 l of water was added thereto. The mixture was agitated for 30 minutes and centrifuged at 3,000 rpm to recover the supernatant. The supernatant was filtered through a filter paper[Toyo No. 4] to obtain filtered solution. The resulting solution was subject to ultrafiltration through PM-10 membrane[Amicon Co. Ltd.]. The filtered solution was freeze-dried and stored. The desired peptides were obtained through series of chromatographies.

chromatography conditions:

Preparative high performance liquid chromatography model LC-20[Japan analytical institute] was used.

Figure 1:
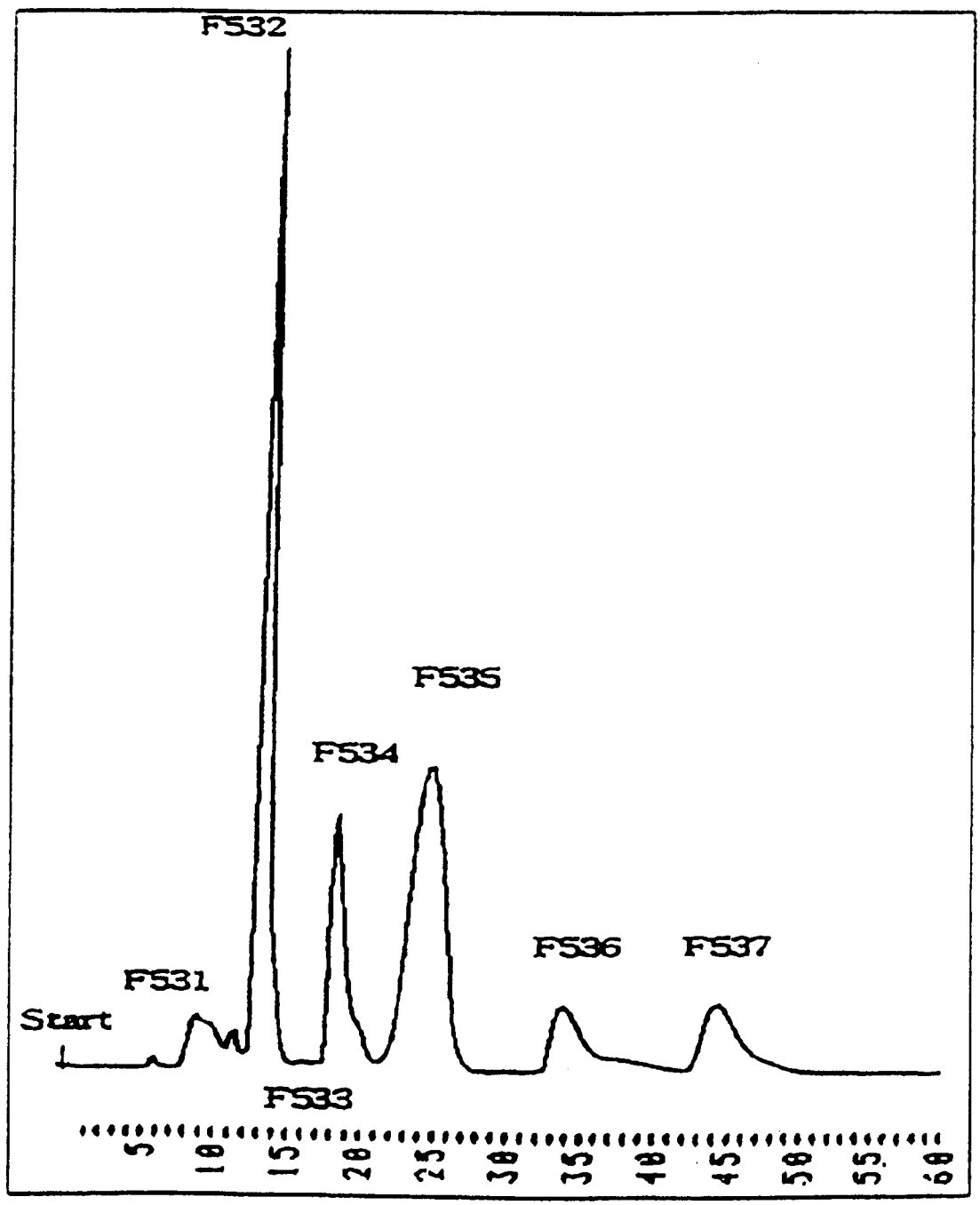
FIG. 1 shows chromatogram obtained after 3rd chromatography during the peptide separation from fermented soybean paste according to the present invention.
Figure 2:
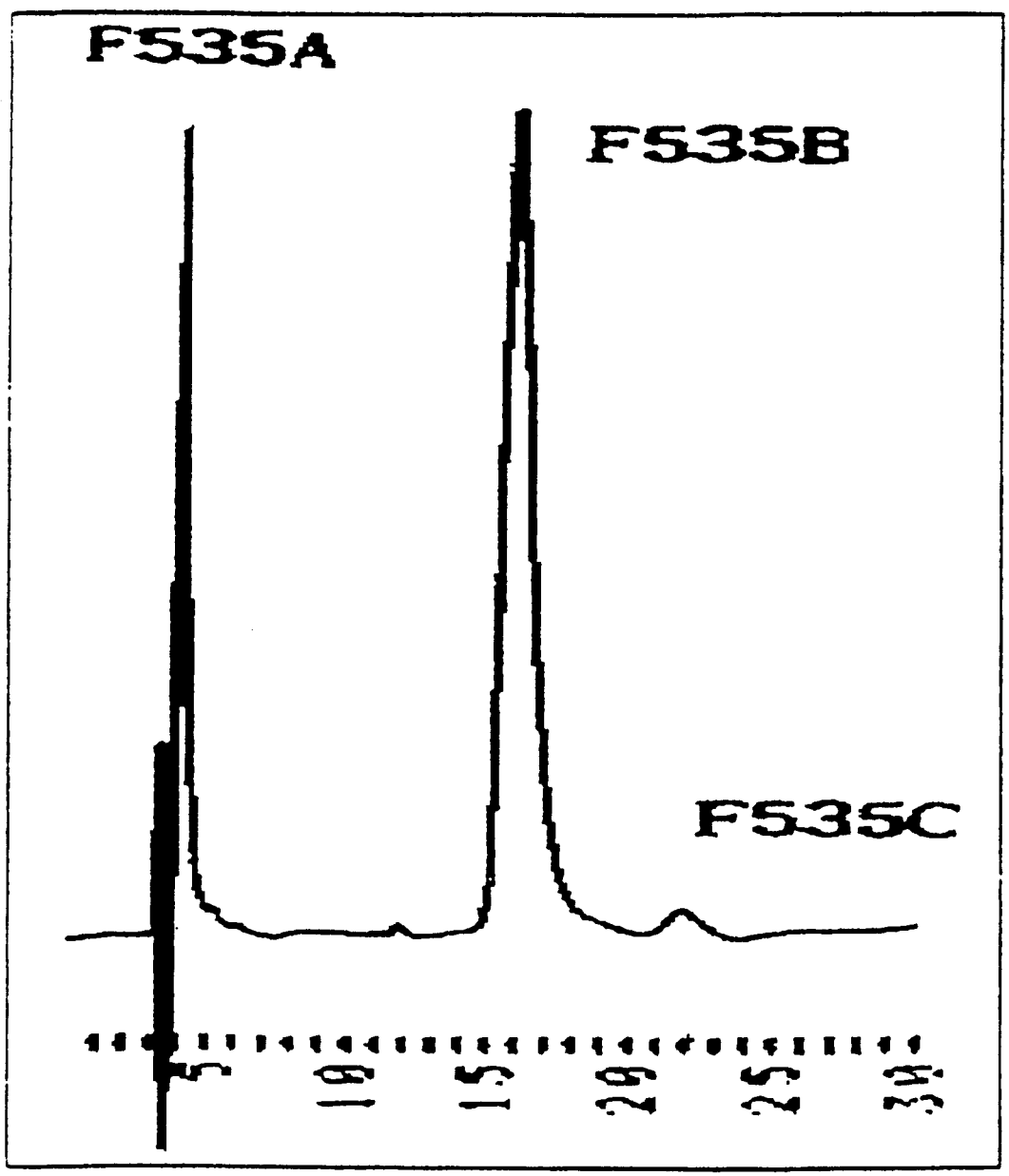
FIG. 2 shows chromatogram obtained after 4th chromatography during the peptide separation from fermented soybean paste according to the present invention.

1] 1st chromatography
JAIGEL-ODS-A-301 column [Japan analytical institute]
mobile phase: 2%~60% acetonitrile; flow rate 5 ml/min
214 nm UV detector 2] 2nd chromatography
JAIGEL-ES-502CP column
mobile phase: 0.1M sodium succinate buffer(pH 4.2); flow rate 4 ml/min
214 nm UV detector 3] 3rd chromatography
JAIGEL-ODS-A-301 column
mobile phase: 10%-acetonitrile containing 0.05%-trifluoroacetic acid; flow rate 1 ml/min
214 nm UV detector 4] 4th chromatography
JAIGEL-ES-502N column
mobile phase: 0.1M Tris-HCl buffer(pH 7.5); flow rate 1 ml/min
214 nm UV detector After the 1st chromatography under the condition mentioned above item 1], 7 eluent fractions were obtained. ACE inhibiting activity of each eluent fraction was measured in accordance with the method by Cushman and Cheung [Biochem. Pharmacol., 20 1637 (1971)]. The activity of the 5th fraction was found highest. The 5th fraction was subject to the 2nd chromatography under the condition mentioned above item 2] and the resulting 5 eluent fractions were evaluated for ACE inhibiting activities. The 3rd fraction was found to have the highest ACE inhibiting activity. This fraction was, in turn, subject to the 3rd chromatography under the condition mentioned above item 3]. The resulting chromatogram is shown in FIG. 1. The 5th eluent fraction exhibited the highest activity. The fraction was used for 4th chromatography under the condition mentioned above item 4]. The resulting chromatogram is shown in FIG. 2. The fractions A and B eluted from the column were analyzed by using protein sequence analyzer and found to contain the tri-peptides according to the present invention, His-His-Leu [1] and His-Leu-Leu[2].

B. Measurement of ACE inhibiting activities of His-His-Leu and His-Leu-Leu

A commercially available ACE was allowed to act on its substrate(HHL) with or without the tri-peptides according to the present invention, and the amount of resulting hippuric acid was measured at 228 nm and adopted as the ACE inhibiting activity. $IC_{50}$, a concentration wherein ACE activity is inhibited by 50% was obtained by using nitrogen analyzer. $IC_{50}$ of His-His-Leu and His-Leu-Leu were 21.8 μg protein/ml, 22.2 μg protein/ml, respectively.

What is claimed is:

1. An ACE inhibitor of the formula I, or a physiologically acceptable salt thereof:

His-His-Leu     (I).

2. The ACE inhibitor according to claim 1, wherein the physiologically acceptable salt is selected from the group consisting of hydrochloride, hydroiodide, sulfate, acetate, citrate, tartrate, lactate and methanesulfonate.

3. The ACE inhibitor according to claim 2, wherein the physiologically acceptable salt is hydrochloride.

4. The ACE inhibitor according to claim 2, wherein the physiologically acceptable salt is hydroiodide.

5. The ACE inhibitor according to claim 2, wherein the physiologically acceptable salt is sulfate.

6. The ACE inhibitor according to claim 2, wherein the physiologically acceptable salt is acetate.

7. The ACE inhibitor according to claim 2, wherein the physiologically acceptable salt is citrate.

8. The ACE inhibitor according to claim 2, wherein the physiologically acceptable salt is tartrate.

9. The ACE inhibitor according to claim 2, wherein the physiologically acceptable salt is lactate.

10. The ACE inhibitor according to claim 2, wherein the physiologically acceptable salt is methanesulfonate.

11. A method for ACE inhibition, comprising the steps of:

selecting an ACE inhibitor of the formula I or II, or a physiologically acceptable salt thereof:

His-His-Leu (I)

His-Leu-Leu (II);

and administering the ACE inhibitor to a human to inhibit ACE.

12. The method according to claim 11, wherein the formula is formula (I).

13. The method according to claim 11, wherein the formula is formula (II).

14. The method according to claim 11, wherein the physiologically acceptable salt is selected from the group consisting of hydrochloride, hydroiodide, sulfate, acetate, citrate, tartrate, lactate and methanesulfonate.

15. The method according to claim 11, wherein the ACE inhibitor is produced from soybean.

* * * * *